United States Patent [19]
Santilli et al.

[11] 3,940,394
[45] Feb. 24, 1976

[54] (2-PYRIMIDINYLTHIO)ALKANOIC ACIDS, ESTERS, AMIDES AND HYDRAZIDES

[76] Inventors: Arthur A. Santilli, Havertown; Anthony C. Scotese, King of Prussia; Rudolph M. Tomarelli, Phoenixville, all of Pa.

[22] Filed: Oct. 24, 1973

[21] Appl. No.: 409,346

Related U.S. Application Data

[62] Division of Ser. No. 240,266, March 31, 1972, Pat. No. 3,814,761.

[52] U.S. Cl............................ 260/256.5 R; 424/251
[51] Int. Cl............................................. C07d 51/40
[58] Field of Search ............................ 260/256.5 R

[56]          References Cited
          UNITED STATES PATENTS
2,347,992   5/1944   D'Alelio et al............... 260/256.5 R
2,352,945   7/1944   D'Alelio et al............... 260/256.5 R
2,621,182  12/1952   Hitchings et al. ........... 260/256.5 R
2,819,965   1/1958   Murray et al. ............... 260/256.5 R Primary Examiner—Albert T. Meyers
Assistant Examiner—Leonard Schenkman
Attorney, Agent, or Firm—Richard K. Jackson

[57]      ABSTRACT (2-Pyrimidinylthio)alkanoic acid, esters, amides and hydrazides as well as various 4- and 6-substituted derivatives thereof as depicted by the structural formula:

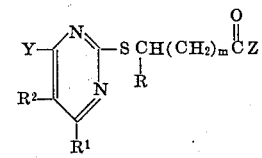

in which R and $R^2$ are independently —H or lower alkyl; $R^1$ is —H, -halo or lower alkoxy; Z is —OH, OM, lower alkoxy or —$(NH)_1$—$NH_2$, wherein $p$ is 0 to 1 and M is an alkali metal, alkaline earth metal or ammonium cation; Y is an aryl, amino or substituted amino radical; and $m$ is an integer from 0 to 2, exhibit anti-lipemic activity in warm-blooded animals.

3 Claims, No Drawings

(2-PYRIMIDINYLTHIO)ALKANOIC ACIDS, ESTERS, AMIDES AND HYDRAZIDES

This is a division of application Ser. No. 240,266, filed Mar. 31, 1972, now U.S. Pat. No. 3,814,761.

BACKGROUND OF THE INVENTION

Anti-lipemic agents in current use include such diverse compounds as ethyl p-chlorophenoxyisobutyrate (clofibrate), ricotinic acid, thyroxine, certain estrogens and the bis(p-chlorophenyl)-acetal of 1-methyl-4-piperidyl glyoxylate.

DESCRIPTION OF THE INVENTION

In accordance with this invention, there is provided certain novel anti-lipemic agents presenting the (2-pyrimidinylthio)alkanoic acid, ester, amide and hydrazide structure, methods for their preparation, pharmaceutical compositions for their administration and methods for their administration to reduce the cholesterol and/or triglyceride content of blood serum.

The compounds of this invention reduce the concentration of triglycerides in blood serum in normal rats, whereas the concentration of triglycerides and cholesterol are reduced in rats on a hypercholesterolemic diet. Thus, the mechanism of action of the compounds of this invention appears to differ from that of the clofibrate type anticholesterolemic agents, which tend to produce a hypocholesterolemic state in normal and hypercholesterolemic blood.

The (2-pyrimidinylthio)alkanoic acids, esters, amides and hydrazides of this invention may be depicted by the structural formula:

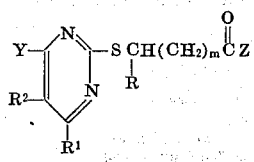

in which

R and $R^2$ are members independently selected from the group consisting of hydrogen and lower alkyl radicals;

$R^1$ is a member selected from the group consisting of hydrogen, halo and lower alkoxy radicals;

Z is a member selected from the group consisting of hydroxy, lower alkoxy, —OM and —(NH)$_p$—NH$_2$ radicals, wherein $p$ is 0 or 1, and M is an alkali metal cation, an alkaline earth metal cation or the ammonium ion;

Y is a member selected from the group consisting of an aryl radical of 6 to 10 carbon atoms;

and

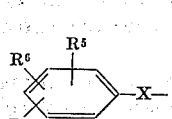

$R^3$ is a hydrogen or lower alkyl radical,
$R^4$ is hydrogen, H$_2$N—,

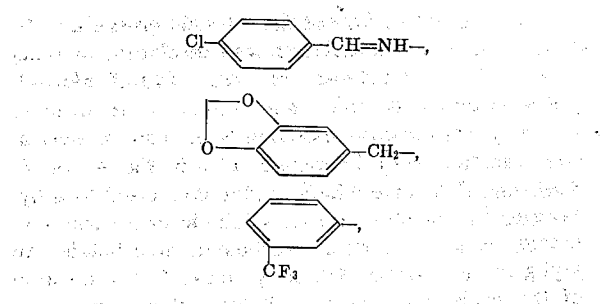

phenyl, (lower)alkoxyphenyl, or di(lower)alkoxyphenyl, providing that when $R^3$ is hydrogen and $R^4$ is hydrogen, phenyl, (lower)alkoxyphenyl or di(lower)alkoxyphenyl, $R^1$ is halo or lower alkoxy $R^5$ is a member selected from the group consisting of a lower alkyl radical, a halo radical, an aryl radical of 6 to 10 carbon atoms and a haloaryl radical of 6 to 10 carbon atoms, $R^6$ is a member selected from the group consisting of hydrogen, lower alkyl, lower alkoxy and halo radicals, $R^7$ is a member selected from the group consisting of hydrogen and lower alkyl radicals, and X is a member selected from the group consisting of

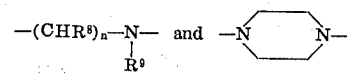

wherein
$R^8$ is hydrogen or lower alkyl,
$R^9$ is hydrogen or lower alkyl, and
$n$ is an integer from 0 to 3.

By the expression "lower," used to modify the terms alkyl and alkoxy, applicants mean to limit the aliphatic chain length of those monovalent, branched and unbranched groups of paraffinic derivation to from 1 to about 6 carbon atoms. By the term "halo" applicants mean to embrace the halogens chlorine, fluorine, iodine and bromine.

The anti-lipemic compounds of this invention may be readily prepared from (4,6-dichloro-2-pyrimidinylthio)alkanoic acid intermediates which themselves are obtained, for example, by converting 2-thiobarbituric acid to the (4,6-dihydroxy-2-pyrimidinylthio)alkanoic acid ester by reaction with an alpha-halo(lower)alkanoic acid ester and subsequently displacing the 4- and 6- positioned hydroxyl groups with chlorine by reaction with an agent such as POCl$_3$, PCl$_5$, and the like. Thus,

I

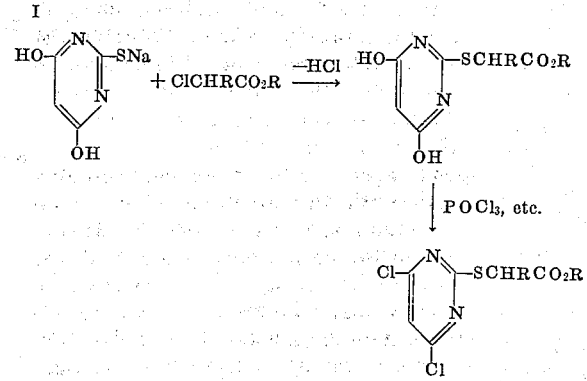

Various modifications of the 4,6-halo groups may be accomplished by substitution and displacement reactions. Thus, reactions of the (4,6-dichloro-2-pyrimidinylthio)alkanoic acid esters with primary amines yields the corresponding 4- or 6-amino derivative, reaction with hydrazine affords the 4- or 6-hydrazino derivative which readily converted to a hydrazone by reaction with an aldehyde or a carbonhydrazide by reaction with a carboxylic acid halide. An aryl group is positioned directly on the 4- or 6-position of the pyrimidine nucleus, if desired, by employing 6-phenyl-2-thiouracil as the initial reactant in lieu of a thio-barbituric acid. From the intermediate monochloro-4 or 6-substituted-2-pyrimidinylthio acetic acid ester, modification of the carboxylic acid functional group is readily achieved by transesterification, saponification and hydrolysis as well as by amidation of the free carboxyl group or the corresponding acid halide.

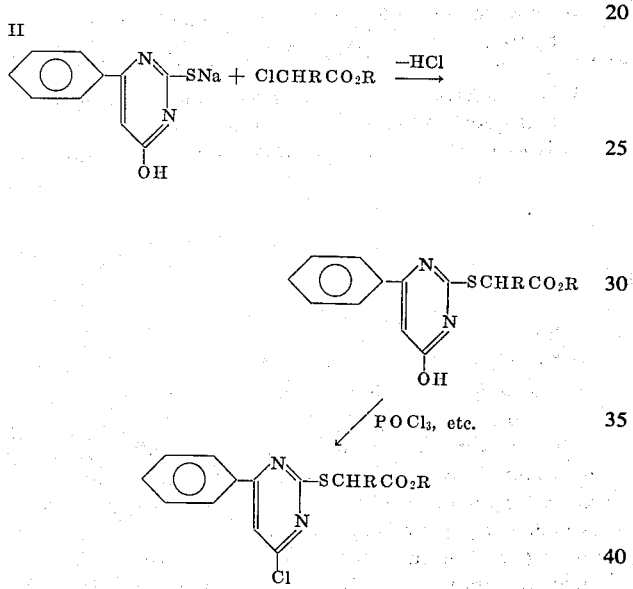

The anti-lipemic activity of the compounds of this invention was established by orally administering the compounds being tested to each member of a group of young male rats which had been fed a hypercholesterolemic diet for three weeks and grouped, based upon their equal average serum cholesterol concentration determined on 0.01 milliliters of serum separated from tail blood collected in a capillary tube. The compounds tested were administered orally once or twice a day for three consecutive days. The serum cholesterol was determined on the fourth day and compared to the average of the group of untreated rays. The potency of the test compound is expressed as the percent activity of concomitantly run tests employing Atromid S (clofibrate) as the standard. The test procedure was repeated with normal chow-fed rats to determine the hypolipemic effect in the normal host.

The hypolipemic agents of this invention are effectively administrable orally or parenterally. The amount of the active compound needed to reduce the fat content of the blood to the desired level varies with the mode of administration to a certain extent as well as the condition of the individual under treatment with regard to age, fat concentration in the blood and depots, diet, transference factors of the gut and interstitial tissues and contributing factors such as the presence of hyperthyroidism, diabetes, cirrhosis of the liver or spleen, pancreatitis, etc.

In practice, the compounds are administered to one suffering from hyperlipemia in unit doses containing from 0.05 to 25 milligrams of active ingredient, the remainder of the formulation constituting known adjuvants. In human treatment, from 1 to 10 milligram and conventionally 5 milligram doses of the active compounds of this invention are considered to be most desirable from the standpoint of uniform presentation for controlled administration. The compounds of the invention may be administered alone or in combination with pharmacologically acceptable carriers, the proportion of which is determined by the chosen route of administration and standard pharmaceutical practice. For example, they may be administered orally in tablet or capsule form with conventional flavors, diluents, lubricants, disintegrators or binding agents as may be required. They may be administered orally in the form of a solution or they may be injected parenterally. For parenteral administration they may be used in the form of a sterile solution containing other solutes, for example, enough saline or glucose to make the solution isotonic.

A suitable tablet formulation is as follows:

| | |
|---|---:|
| [4-Chloro-6-(2,3-xylindino)-2-pyrimidinylthiol acetamide | .05 mg |
| microcrystallire Cellulose, N.F. | .20 mg |
| Magnesium Stearate, U.S.P. | 25.00 mg |
| Lactose, U.S.P. | 74.75 mg |
| Total Weight | 100 mg |

A suitable formulation for parenteral administration is as follows:

| | |
|---|---:|
| Sodium[4-Chloro-6-(2,3-xylidino)-2-pyrimidinylthio]acetate | 5 mg |
| Vehicle: sterile water, containing benzyl alcohol (1 percent) and sodium acetate-acetic acid buffer 0.6% | 5 ml. |

The compounds of this invention which exhibit markedly superior anti-lipemic activity when compared to the standard Atromid S in the test procedure, are those compounds of the formula:

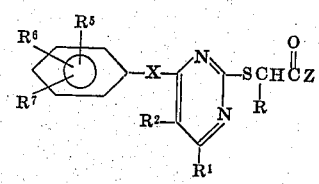

in which
R¹ is a member selected from the group consisting of hydrogen and chloro radicals;
R, R² and R⁷ are members independently selected from the group consisting of hydrogen and lower alkyl radicals;
R⁵ is selected from the group consisting of lower alkyl; lower alkoxy, aryl of 6 to 10 carbon atoms, haloaryl of 6 to 10 carbon atoms and halo radicals;
R⁶ is selected from the group consisting of —H, lower alkyl, halo and lower alkoxy radicals;
X is selected from the group consisting of

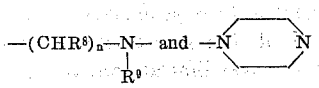

wherein $R^8$ and $R^9$ are independently —H or lower alkyl and $n$ is an integer from 0 to 3, providing that when n is 0 and $R^5$ is lower alkoxy, $R^6$ is lower alkyl, lower alkoxy or halo; and Z is selected from the group consisting of —OH, OM, lower alkoxy and —(NH)$_p$—NH$_2$, in which $p$ is an integer from 0 to 1 and M is an alkali metal, alkaline earth metal or ammonium cation.

Of these compounds those exhibiting the greatest activity are the [4-chloro-6-arylamino-2-pyrimidinylthio] acetic acid, alkali metal salt, amide, hydrazide and lower alkyl ester in which the aryl group contains from 7 to 12 carbon atoms, and the 6-parachlorophenylamino and 6-parachlorobenzylamino analogues thereof.

The compounds embraced by the above structural formula exhibit antihypercholesterolemic activity from 2 to 26 times in excess of that exhibited by Atomid S brand of clofibrate in concomitantly run studies on groups of young male rats which had been previously fed a hypercholesterolemic diet. The antilipemic activity of the compounds of this invention was established by the determination of a quantitative reduction of serum cholesterol concentration determined on the fourth day after oral administration of the active compounds once or twice a day for three days to the rats grouped on the basis of equal average serum cholesterol.

The compounds of this invention which exhibit positive antihypercholesterolemic activity to a degree equal to or below that of the standard clofibrate employed in the test procedures (Atromid S) may be represented by the formula:

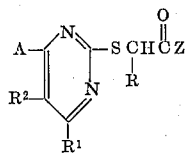

in which

A is a member selected from the group consisting of aryl of 6 to 10 carbon atoms and

wherein $R^9$ is —H or lower alkyl and $R^{10}$ is hydrogen, H$_2$N—,

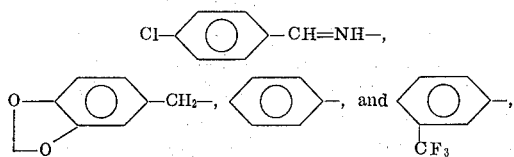

R is selected from the group consisting of —H and lower alkyl;

$R^2$ is selected from the group consisting of —H and lower alkyl;

$R^1$ is selected from the group consisting —H, chloro and lower alkoxy radicals, with the proviso that when A is the amino or phenylamino group $R^1$ is chloro or lower alkoxy; and Z is selected from the group consisting of —NHNH$_2$, lower alkoxy, —OH and OM, wherein M is an alkali metal, alkaline earth metal or ammonium cation.

The following Examples are presented to illustrate the procedure employed to produce the compounds of this invention and are not to be construed in themselves as limitations upon the true scope of the subject matter applicants regard as their invention.

EXAMPLE I (4,6-Dichloro-2-pyrimidinylthio)acetic acid, ethyl ester

To a solution of 8.4 g (0.1 mole) of sodium bicarbonate in 500 ml. of water was added with stirring 14.4 g (0.1 mole) of 2-thiobarbituric acid. Ethyl bromoacetate (16.7 g, 0.1 mole) was then added with enough ethanol to make a clear solution. Within one-half hour a precipitate was formed. Stirring was continued for 2 hr. at room temperature. The precipitate amounted to 20.2 g. Recrystallization from ethanol gave the analytical sample mp. 194°–197°C., of (4,6-Dihydroxy-2-pyrimidinylthio)acetic acid, ethyl ester.

Anal. Calcd for C$_8$H$_{10}$N$_2$O$_4$S: C, 41.73; H, 4.38; N, 12.15.

Found: C, 41.75; H, 4.46; N, 12.27.

To a mixture of 73.6 g of (4.6-dihydroxy-2-pyrimidinylthio)acetic acid, ethyl ester in 500 ml. of phosphorus oxychloride was slowly added 47.7 g of N,N-diethylaniline. After the heat generated by this addition had abated the reaction mixture was heated under reflux for 5 hr. The phosphorus oxychloride was removed in a rotary evaporator and the residue was poured onto 2-liters of ice water. The reaction mixture was allowed to stand for 3 days and was filtered. The filter cake was recrystallized from petroleum ether giving 61.0 g of product. Recrystallization a second time from petroleum ether gave an analytical sample; mp. 61°–62°C., of the title compound.

Anal. Calcd for C$_8$H$_8$Cl$_2$N$_2$O$_2$S: C, 35.97; H, 3.02; N, 10.48.

Found: C, 35.95; H, 3.00; N, 10.30.

EXAMPLE 2

(4-Amino-6-chloro-2-pyrimidinylthio)acetic acid ethyl ester

A mixture of 10.7 g of (4,6-dichloro-2-pyrimidinylthio) acetic acid, ethyl ester and 4.2 g of sodium carbonate in 150 ml. of saturated ethanolic ammonia solution was stirred at room temperature for 1 week. The reaction mixture was filtered and petroleum ether was added to the filtrate until a precipitate was formed. The precipitate was recrystallized from petroleum ether-ethanol to give 1.2 g of product, mp. 113°–116°C.

Anal. Calcd for C$_8$H$_{10}$N$_3$O$_2$SCl: C, 38.78; H, 3.07; N, 16.96; Cl, 14.50.

Found: C, 38.96; H, 4.09; N, 17.16; Cl, 14.57.

EXAMPLE 3

(4-Anilino-6-chloro-2-pyrimidinylthio)acetic acid ethyl ester

A stirred mixture of 8.0 g of (4,6-dichloro-2-pyrimidinylthio)acetic acid ethyl ester, 2.8 g of aniline and 3.2 g of sodium carbonate in 100 ml. of ethanol was heated under reflux for 5 hr. The reaction mixture was filtered and water was added to the filtrate to start precipitation. The crude product was recrystallized from 95% ethanol to afford 6.7 g of product, mp. 109°–114°C.

Anal. Calcd for $C_{14}H_{14}N_3ClSO_2$: C, 51.93; H, 4.36; N, 12.98.

Found: C, 51.69; H, 4.15; N, 13.27.

EXAMPLE 4

(4-Chloro-6-(p-chloroanilino)-2-pyrimidinylthio)acetic acid ethyl ester

A stirred mixture of 8.0 g of (4,6-dichloro-2-pyrimidinylthio)acetic acid ethyl ester, 3.8 g of p-chloroaniline and 3.2 g of sodium carbonate in 100 ml. of ethanol was heated under reflux for 5 hr. The reaction mixture was filtered and water was added to the filtrate until precipitation resulted. Recrystallization of this material from 95% ethanol afforded 3.0 g of product, mp. 109°–112°C.

Anal. Calcd for $C_{14}H_{13}N_3SO_2CL_2$: C, 46.94; H, 3.66; N, 11.73.

Found: C, 46.65; H, 3.77; N, 11.75.

EXAMPLE 5

[4-Chloro-6-(p-fluoroanilino)-2-pyrimidinylthio]acetic acid ethyl ester

A stirred mixture of 10.7 g of (4,6-dichloro-2-pyrimidinylthio)acetic acid ethyl ester, 4.4 g of p-fluoroaniline and 4.2 g of sodium carbonate was heated under reflux for 6 hr. and filtered. Water was added to the filtrate to the precipitation point. The precipitate was removed by filtration and recrystallized from 95% ethanol to afford 4.1 g of product; mp. 97°–102°C.

Anal. Calcd for $C_{14}H_{13}N_3ClFSO_2$: C, 49.19: H, 3.83; N, 12.29.

Found: C, 48.92; H, 4.00; N, 12.39.

EXAMPLE 6

[4-Chloro-6-($\alpha,\alpha,\alpha$-trifluoro-m-toludino)-2-pyrimidinylthio]acetic acid ethyl ester A mixture of 5.2 g of 3-amino benzotrifluoride, 8.5 g of (4,6-dichloro-2-pyrimidinylthio)acetic acid ethyl ester, 3.4 g of sodium carbonate and 100 ml of ethanol were heated to 135°C. for 5 hr. in an autoclave. The reaction mixture was cooled in ice and filtered. Water was added to the filtrate to start precipitation. The solid was collected and recrystallized from 95% ethanol giving 3.3 g of product, mp. 110°–114°C.

Anal. Calcd for $C_{15}H_{13}N_3ClF_3O_2S$: C, 45.98: H, 3.34; N, 10.72.

Found: C, 45.90; H, 3.22; N, 10.64.

EXAMPLE 7

[4-Chloro-6-(2,3-xylidino)-2-pyrimidinylthio]acetic acid ethyl ester

A stirred mixture of 2.7 g of (4.6-dichloro-2-pyrimidinylthio)acetic acid, ethyl ester, 1.2 g of 2,3-dimethylaniline and 1.06 g of anhydrous sodium carbonate in 20 ml. of ethanol was heated under reflux for 4 hr. The mixture was filtered and water added to the filtrate until a precipitate appeared. The solid was recrystallized from 95% ethanol to a mp. of 88°–93°C.

Anal. Calcd for $C_{16}H_{18}N_3O_2ClS$: C, 54.62: H, 5.15; N, 11.94.

Found: C, 54.80; H, 5.08; N, 12.00.

EXAMPLE 8

[4-Chloro-6-(2,4,6-trimethylanilino)-2-pyrimidinylthio] acetic acid ethyl ester

A mixture of 5.3 g of (4,6-dichloro-2-pyrimidinylthio) acetic acid ethyl ester, 2.7 g of 2,4,6-trimethylaniline and 2.1 g of sodium carbonate in 50 ml. of ethanol was heated in an autoclave to 200°C. for 5 hr. The reaction mixture was filtered and water was added to initiate precipitation. The precipitate was removed by filtration and recrystallized from 95% ethanol to afford 3.2 g of product, mp. 100–103°C.

Anal. Calcd for $C_{17}H_{20}N_3ClSO_2$: C, 55.80; H, 5.51; N, 11.48.

Found: C, 55.57; H, 5.38; N, 11.21.

EXAMPLE 9

[4-Chloro-6-(p-methoxyanilino)-2-pyrimidinylthio]acetic acid ethyl ester

A stirred mixture of 5.2 g of (4,6-dichloro-2-pyrimidinylthio)acetic acid ethyl ester, 2.4 g of p-anisidine and 2.1 g of sodium carbonate in 100 ml. of ethanol was heated under reflux for 6 hr. The reaction mixture was filtered and the filtrate cooled in ice. A crystalline material was deposited which was purified by recrystallization from ethanol. There was obtained 4.5 g of product, mp. 96°–97.5°C.

Anal. Calcd for $C_{15}H_{16}N_3ClSO_3$: C, 50.92; H, 4.56; N, 11.87.

Found: C, 51.16; H, 4.77; N, 12.00.

EXAMPLE 10

[4-(4-Biphenylylamino)-6-chloro-2-pyrimidinylthio]acetic acid ethyl ester

A stirred mixture of 5.3 g of (4,6-dichloro-2-pyrimidinylthio)acetic acid ethyl ester, 3.4 g of 4-aminobiphenyl and 2.1 g of sodium carbonate in 100 ml. of ethanol was heated under reflux for 5 hr. The reaction mixture was filtered and water was added to the filtrate to initiate precipitation. The precipitate was recrystallized from ethanol to give 3.1 g of product, mp. 110°–112°C.

Anal. Calcd for $C_{20}H_{18}N_3ClSO_2$: C, 58.83; H, 4.68; N, 10.83.

Found: C, 58.72; H, 4.60; N, 10.71

EXAMPLE 11

(4-Chloro-6-[4-(p-chlorphenyl)-1-piperazinyl]-2-pyrimidinylthio)acetic acid ethyl ester A mixture of 5.3 g of (4,6-dichloro-2-pyrimidinylthio) acetic acid ethyl ester, 3.9 g of N-(p-chlorophenyl)piperazine and 2.1 g of sodium carbonate in 120 ml. of ethanol was warmed on a steam bath for 10 minutes. The reaction mixture was filtered and the filtrate was diluted with water in order to cause precipitation. The precipitate was recrystallized from ethanol to afford 5.3 g of product, mp. 117°–120°C.

Anal. Calcd for $C_{18}H_{20}N_4SCl_2O_2$: C, 50.59; H, 4.72; N, 13.11.
Found: C, 50,96; H, 4.99; N, 13.17.

EXAMPLE 12

[4-Chloro-6-(2,3-xylidino)-2-pyrimidinylthio]acetic acid

A mixture of 21.4 g of (4,6-dichloro-2-pyrimidinylthio) acetic acid ethyl ester, 9.7 g of 2,3-dimethylaniline, 8.5 g of anhydrous sodium carbonate in 200 ml. of ethanol was heated under reflux with stirring for 4 hr. The mixture was filtered and water was added to the filtrate until precipitation occurred. This material was removed by filtration and amounted to 7.0 g. This material was treated with boiling 30% sodium hydroxide solution (30 ml.) and sufficient ethanol to obtain a clear solution. After cooling in ice the material was acidified with 30% hydrochloric acid solution. The resulting product was then recrystallized from ethanol giving 4.3 g of product, mp. 146°–151°C.

Anal. Calcd for $C_{14}H_{14}N_3ClO_2S$: C, 51.93; H, 4.36; N, 12.98.
Found: C, 51.65; H, 4.31; N, 13.18.

EXAMPLE 13

[4-Chloro-6-(2,3-xylidino)-2-pyrimidinylthio]acetamide 5.0 g of [4-chloro-6-(2,3-xylidino)-2-pyrimidinylthio] acetic acid, ethyl ester was added to 40 ml of concentrated ammonium hydroxide. Ethanol (40 ml) was then added and the reaction mixture was boiled to give a clear solution. This solution then stood at room temperature for three days. The precipitate thus formed was collected and recrystallized from ethanol giving 3.0 g of product, mp. 188°–191°C.

Anal. Calcd for $C_{14}H_{15}N_4OClS$: C, 52.09; H, 4.68; N, 17.36.
Found: C, 51.77; H, 4.89; N, 17.18.

EXAMPLE 14

[4-Chloro-6-(2,3-xylidino)-2-pyrimidinylthio]acetic acid hydrazide

A mixture of 5.0 g of [4-chloro-6-(2,3-xylidino)-2-pyrimidinylthio]acetic acid ethyl ester and 5.0 g of hydrazine hydrate (98%) in 40 ml. of ethanol was allowed to stand overnight at room temperature. Water was added to the mixture until a precipitate appeared. This material was recrystallized from ethanol affording 4.8 g of product, mp. 185°–189°C.

Anal. Calcd for $C_{14}H_{16}N_5OClS$: C, 49.77, H, 4.77; N, 20.73.
Found: C, 49.54; H, 5.10; N, 20.74.

EXAMPLE 15

[4-Chloro-6-(p-chlorobenzylamino)-2-pyrimidinylthio]acetic acid, ethyl ester

A stirred mixture of 10.63 g of p-chlorobenzylamine, 7.54 g of anhydrous sodium carbonate and 20.04 g of (4,6-dichloro-2-pyrimidinylthio)acetic acid, ethyl ester in 250 ml. of ethanol was heated under reflux for 4 hr. The reaction mixture was filtered and water was added to the filtrate until a precipitate was formed. The product amounted to 21.5 g; mp. 82°–85°C. The analytical sample was obtained by recrystallization from benzene-petroleum ether, mp. 82°–84.5°C.

Anal. Calcd for $C_{15}H_{15}N_3Cl_2O_2S$: C, 48.39; H, 4.06; N, 11.29.
Found: C, 48.24; H, 4.01; N, 11.33.

EXAMPLE 16

[4-Chloro-6(p-fluorobenzylamino)-2-pyrimidinylthio]acetic acid, ethyl ester

A stirred mixture of 3.75 g of p-fluorobenzylamine, 3.18 g of anhydrous sodium carbonate and 8.01 g of (4-,6-dichloro-2-pyrimidinylthio)acetic acid, ethyl ester in 150 ml of ethanol was heated under reflux for 5 hr. The reaction mixture was filtered and water was added to the filtrate until a precipitate was formed. The solid was collected and recrystallized from benzene-petroleum ether giving 3.6 g of product, mp. 70°–75°C.

Anal. Calcd for $C_{15}H_{15}N_3ClSO_2F$: C, 50.63; H, 4.25; N, 11.81.
Found: C, 50.38; H, 4.26; N, 11.83.

EXAMPLE 17

[4-Chloro-6-(3,4-dichlorobenzylamino)-2-pyrimidinylthio] acetic acid

A stirred mixture of 8.0 g of (4,6-dichloro-2-pyrimidinylthio)acetic acid ethyl ester, 5.3 g of 3,4-dichlorobenzylamine and 3.2 g of sodium carbonate in 200 ml. of ethanol was heated under reflux for 6 hr. The reaction mixture was filtered and water was added to the filtrate to the cloudy point. The mixture was cooled in ice and the resulting precipitate which formed was removed by filtration and recrystallized from 70% aqueous ethanol. The product amounted to 4.8 g, mp. 64°–69°C.

Anal. Calcd for $C_{15}H_{14}N_3Cl_3SO_2$: C, 44.30; H, 3.47; N, 10.33.
Found: C, 44.26; H, 3.50; N, 10.24.

EXAMPLE 18

[4-Chloro-6-(2,4-dimethoxyanilino)-2-pyrimidinylthio]acetic acid

A stirred mixture of 10.7 g of (4,6-dichloro-2-pyrimidinylthio)acetic acid ethyl ester, 6.1 g of 2,4-dimethoxyaniline and 4.24 g. of sodium carbonate in 100 ml. of ethanol was heated under reflux for 5 hr. The reaction mixture was filtered and the filtrate taken to dryness in a rotary evaporator. The residue was boiled for 3 minutes with approximately 10 ml. of 30% sodium hydroxide solution and a sufficient quantity of ethanol to obtain a clear solution. The mixture was acidified with concentrated hydrochloric acid solution. An oil was obtained. The supernatant liquid was decanted and the oil was dissolved in 30% aqueous base. Re-acidification with concentrated hydrochloric acid caused a precipitate to deposit. The material was recrystallized from ethanol-petroleum ether giving 3.6 g of product, mp. 130°–134°C.

Anal. Calcd for $C_{14}H_{14}N_3ClO_4S$: C, 47.26; H, 3.96; N, 11.81.
Found: C, 47.01; H, 4.02; N, 12.02.

EXAMPLE 19

[4-Chloro-6-(2,4-dimethylbenzylamino)-2-pyrimidinylthio] acetic acid ethyl ester A stirred mixture of 5.3 g of (4,6-dichloro-2-pyrimidinylthio)acetic acid ethyl ester, 2.7 g of 2,4-dimethylbenzylamino and 2.1 g of sodium carbonate in 35 ml. of ethanol was heated under reflux for 5 hr. The reaction mixture was filtered and the filtrate diluted with petroleum ether until a precipitate formed. This material was recrystallized from petroleum ether-ethanol giving 2.5 g of product, mp. 95°–98°C.

Anal. Calcd for $C_{17}H_{20}N_3O_2ClS$: C, 55.80; H, 5.51; N, 11.48.

Found: C, 55.46; H, 5.22; N, 11.50.

EXAMPLE 20

[4-Chloro-6-(p-chlorophenethylamino)-2-pyrimidinylthio]acetic acid ethyl ester

A mixture of 10.7 g of (4,6-dichloro-2-pyrimidinylthio] acetic acid ethyl ester, 6.2 g of p-chlorophenethylamine, and 4.24 g of sodium carbonate in 150 ml. of ethanol was heated under reflux for 15 minutes. The reaction mixture was filtered and the filtrate was cooled in ice. The crystalline product which was deposited was collected and recrystallized from ethanol giving 3.6 g of product, mp. 105°–108°C.

Anal. Calcd for $C_{16}H_{17}N_3Cl_2O_2S$: C, 49.75; H, 4.44; N, 10.88.

Found: C, 49.81; H, 4.51; N, 10.84.

EXAMPLE 21

(4-Chloro-6[(p-chlorobenzyl)methylamino]-2-pyrimidinylthio) acetic acid ethyl ester A mixture of 13.4 g of (4,6-dichloro-2-pyrimidinylthio) acetic acid ethyl ester, 7.8 g of N-methyl-p-chlorobenzylamine and 5.4 g of sodium carbonate in 100 ml. of ethanol was heated under reflux for 5 hr. The reaction mixture was filtered and the filtrate taken to dryness in a rotary evaporator. The residual oil was dissolved in a minimum quantity of ethanol. The addition of a few drops of water to this solution caused a precipitate to deposit. The precipitate was removed by filtration and recrystallized from ethanol affording 5.8 g of product, mp. 68°–70°C.

Anal. Calcd for $C_{16}H_{17}N_3Cl_2SO_2$: C, 49.75; H, 4.44; N, 10.87.

Found: C, 49.69; H, 4.61; N, 11.09.

EXAMPLE 22

[4-Chloro-6-(p-chloro-α-methylbenzylamino)-2-pyrimidinylthio] acetic acid

A stirred mixture of 2.7 g of (4,6-dichloro-2-pyrimidinylthio)acetic acid ethyl ester, 1.6 g of p-chloro-α-methylbenzylamine and 1.1 g of sodium carbonate in 120 ml. ethanol was heated under reflux for 2 hr. The reaction mixture was filtered and the filtrate taken to dryness in a rotary evaporator in vacuo. The residual oil was treated with 100 ml. of 30% sodium hydroxide solution containing a few ml. of ethanol. After a few minutes the clear solution was acidified with concentrated hydrochloric acid and the mixture thus formed was extracted with ether (3 × 50 ml.). The ether solution was dried over magnesium sulfate, filtered and the filtrate evaporated to dryness. The residue was dissolved in 50 ml. of benzene and petroleum ether was added until the solution became cloudy. On cooling in ice a precipitate was deposited. Recrystallization of this material from 50% aqueous ethanol afforded the product, mp. 155°–160°C.

Anal. Calcd for $C_{14}H_{13}N_3Cl_2O_2S$: C, 46.94; H, 3.66; N, 11.73.

Found: C, 47.09; H, 3.84; N, 11.74.

EXAMPLE 23

(4-Chloro-6-[3,4-(methylenedioxy)benzylamino]-2-pyrimidinylthio)acetic acid ethyl ester A stirred mixture of 5.3 g of (4,6-dichloro-2-pyrimidinylthio)acetic acid ethyl ester, 3.0 g of piperonylamine and 2.1 g of sodium carbonate in 100 ml. of ethanol was heated under reflux for 5 hr. The reaction mixture was filtered and water was added to the filtrate to intiate precipitation. The precipitate was removed by filtration and recrystallized from ethanol to afford 5.3 g of product, mp. 75°–79°C.

Anal. Calcd for $C_{16}H_{16}N_3O_4ClS$: C, 50.33; H, 4.22; N, 11.00.

Found: C, 50.62; H, 4.39; N, 10.98.

EXAMPLE 24

[4-Chloro-6-(p-chlorobenzylidenehydrazino)-2-pyrimidinylthio] acetic acid ethyl ester To a solution of 2.1 g of p-chlorobenzaldehyde in 25 ml. of glacial acetic acid was added a solution of 3.9 g of (4-chloro-6-hydrazino-2-pyrimidinylthio) acetic acid ethyl ester in 100 ml. of glacial acetic acid. The reaction mixture was warmed on a steam bath for a few minutes and then cooled in ice. The resulting precipitate was collected, washed with petroleum ether and recrystallized twice from ethanol affording 3.6 g of product, mp. 162°–165°C.

Anal. Calcd for $C_{15}H_{14}N_4Cl_2O_2S$: C, 46.76; H, 3.66; N, 14.54.

Found: C, 46.48; H, 3.59; N, 14.59.

EXAMPLE 25

(4-Chloro-6-[(p-fluorobenzylidene)hydrazino]-2-pyrimidinylthio]acetic acid ethyl ester To a solution of 5.2 g of (4-chloro-6-hydrazino-2-pyrimidinylthio) acetic acid, ethyl ester in 100 ml. of glacial acetic acid was added 2.5 g of p-fluorobenzaldehdye. The reaction mixture was warmed for a few minutes on a steam bath. The resulting precipitate which formed was washed with petroleum ether and recrystallized from ethanol affording 2.7 g of product, mp. 146°–149°C.

Anal. Calcd for $C_{15}H_{14}N_4O_2ClFS$: C, 48.85; H, 3.82; N, 15.19.

Found: C, 48.64; H, 3.92; N, 15.22.

EXAMPLE 26

(4-Chloro-6-hydrazino-2-pyrimidinylthio)acetic acid ethyl ester, hydrochloride

A mixture of 8.01 g of (4,6-dichloro12-pyrimidinylthio) acetic acid ethyl ester, 3.18 g of anhydrous sodium carbonate and 1.5 g of 98% hydrazine hydrate in 150 ml. of absolute ethanol was heated with stirring under reflux for 20 minutes. The hot reaction mixture was filtered and the filtrate was cooled in ice. There was obtained 4.9 g of a precipitate. This material was then treated with 20 ml. of concentrated hydrochloric acid solution. The acid solution was diluted with water and the precipitate which resulted was recrystallized from ethanol-petroleum ether affording 4.9 g of product, mp. 208°C. decomp.

Anal. Calcd for $C_8H_{12}N_4Cl_2O_2S$: C, 32.11; H, 4.04; N, 18.73.

Found: C, 32.19; H, 4.18; N, 18.90.

EXAMPLE 27

[4-Chloro-6-(p-chlorobenzylamino)-2-pyrimidinylthio]acetic acid

[4-Chloro-6-(p-chlorobenzylamino)-2-pyrimidinylthio]acetic acid ethyl ester (1.4 g) was heated for 5 minutes with 30 ml. of 30% sodium hydroxide solution on a hot plate. The reaction mixture was then cooled and acidified with concentrated hydrochloric acid solution. The resulting precipitate was removed by filtration, washed with water and recrystallized from ethanol to afford 1.0 g of product, mp. 211°–213°C., decomp.

Anal. Calcd for $C_{13}H_{11}N_3Cl_2O_2S$: C, 45.35; H, 3.22; N, 12.21.
Found: C, 45.61; H, 3.40; N, 11.95.

EXAMPLE 28

(4-Chloro-6-(p-chlorobenzylamino)-2-pyrimidinylthio)acetic acid hydrazide

A stirred mixture of 1.1 g of (6-chloro-4-p-chlorobenzylamino-2pyrimidinylthio)acetic acid, ethyl ester 0.18 g of hydrazine hydrate (98%) and 0.3 g of sodium carbonate in 15 ml. of ethanol was heated under reflux for 3 hr. The reaction mixture was filtered and the filtrate diluted with water until a precipitate appeared. The solid was washed with aqueous (10%) sodium carbonate then recrystallized from ethanol to a mp. of 178-182°C.

Anal. Calcd for $C_{13}H_{13}N_5OCl_2S$: C, 43.58; H, 3.66; N, 19.55.
Found: C, 43.76; H, 3.87; N, 19.58.

EXAMPLE 29

2-(4,6-Dichloro-2-pyrimidinylthio)propionic acid ethyl ester

To a solution of 21 g of sodium bicarbonate in 500 ml. of water was added in portions 36 g of thiobarbituric acid. Ethanol (25ml.) was added and the resulting solution was heated on a steam bath. Ethyl 2-bromopropionate (45 g) was added and the reaction mixture was heated an additional hour. The mixture was diluted with water and the resulting precipitate was removed by filtration. The precipitate was washed with ether and then recrystallized from ethyl acetate-petroleum ether giving 4.1 g of 2-(4,6-dihydroxy-2-pyrimidinylthio)propionic acid ethyl ester, mp. 164°–167°C. decomp.

Anal. Calcd for $C_9H_{12}N_2O_4S$: C, 44.25; H, 4.95; N, 11.47.
Found: C, 44.24; H, 5.19; N, 11.34.

A mixture of 12.8 g of 2-(4,6-dihydroxy-2-pyrimidihylthio) propionic acid ethyl ester and 7.8 g of diethylaniline in 100 ml. of phosphorus oxychloride was heated under reflux for 6 hr.. The excess phosphorus oxychloride was removed in a rotary evaporator and the residue was poured onto a mixture of ice and water. The mixture was extracted with ether (3 × 150 ml.) and the ether phase was washed with water (100 ml.), 10% sodium bicarbonate (100 ml.) and again with water. The washed ether phase was dried over magnesium sulfate, filtered and taken to dryness. The title compound as a residual oil (8.2 g) was used without further purification in the following Example.

EXAMPLE 30

2-[4-Chloro-6-(p-chlorobenzylamino)-2-pyrimidinylthio]propionic acid

A stirred mixture of 5.6 g of 2-(4,6-dichloro-2-pyrimidinylthio) propionic acid ethyl ester, 2.9 g of p-chlorobenzylamine and 2.1 g of anhydrous sodium carbonate in 50 ml. of ethanol were heated under reflux for 6 hr. The reaction mixture was filtered and taken to dryness on a rotary evaporator. The residue was dissolved in ether and filtered free of insoluble material. The ether was removed on a rotary evaporator and the residue was treated with approximately 10 ml. of 30% sodium hydroxide solution to which was added enough ethanol until a clear solution was obtained. The reaction mixture was heated on a steam bath for a few minutes then acidified with concentrated hydrochloric acid solution. The precipitate which was formed was recrystallized from 95% ethanol affording 5.0 g of product, mp. 133°–136°C.

Anal. Calcd for $C_{14}H_{14}N_3O_2Cl_2S$: C, 46.94; H, 3.66; N, 11.73.
Found: C, 46.79; H, 3.80; N, 11.70.

EXAMPLE 31

(4-Chloro-6-phenyl-2-pyrimidinylthio)acetic acid ethyl ester

To a stirred solution of 8.4 g of sodium bicarbonate in 450 ml. of water and 100 ml. of ethanol was added 20.4 g of 6-phenyl-2-thiouracil. The mixture was heated on a hot plate until a clear solution was obtained then 16.7 g of ethyl bromoacetate was added. A precipitate was deposited which was removed by filtration and washed with water. The dried product amounted to 28.1 g, mp. 214°–218°C. decomp. The analytical sample of (4-hydroxy-6-phenyl-2-pyrimidinylthio)acetic acid ethyl ester was obtained by recrystallization from dimethyl formamide, mp. 217°–219°C.

Anal. Calcd for $C_{14}H_{14}N_2O_3S$: C, 57.92; H, 4.86; N, 9.65.
Found: C, 58.04; H, 5.05; N, 9.79.

A solution of 18.0 g of (4-hydroxy-6-phenyl-2-pyrimidinylthio)acetic acid ethyl ester in 200 ml. of phosphorus oxychloride was heated under reflux for 17 hr. The excess phosphorus oxychloride was removed in a rotary evaporator. The residual oil crystallized on standing. Recrystallization from petroleum ether afforded 8.7 g of the title compound, mp. 82°–84°C.

Anal. Calcd for $C_{14}H_{13}ClN_2O_2S$: C, 54.46; H, 4.24; N, 9.07; S, 10.38; Cl, 11.48.
Found: C, 54.17; H, 4.27; N, 9.39; S, 10.41; Cl, 11.76.

EXAMPLE 32

(4-Methoxy-6-phenyl-2-pyrimidinylthio)acetic acid

To a solution of 0.46 g of sodium metal in 50 ml. of absolute methanol was added 3.2 g of (4-chloro-6-phenyl-2-pyrimidinylthio)acetic acid ethyl ester as prepared in the preceding Example. The reaction mixture was heated under reflux for 3 hr. then filtered. The filtrate was taken to dryness in a rotary evaporator. The residue was dissolved in 30 ml. of 50% sodium hydroxide and the solution was diluted to 200 ml. The reaction mixture was allowed to stand at room temperature for 1.5 hr, cooled in ice and acidified with concentrated hydrochloric acid. The resulting precipitate was recrystallized from aqueous ethanol affording 1.4 g of product, mp. 157°–159°C.

Anal. Calcd for
$C_{13}H_{12}N_2O_3S$: C, 56.52; H, 4.38; N, 10.14; S, 11.58.
Found: C, 56.69; H, 4.77; N, 10.35; S, 11.76.

EXAMPLE 33

[4-(p-Chlorobenzylamino)-2-pyrimidinylthio]acetic acid ethyl ester

A stirred mixture of 32.1 g of (4-hydroxy-2-pyrimidinylthio)acetic acid, ethyl ester and 22.4 g of N,N-diethylaniline in 400 ml. of phosphorus oxychloride were heated under reflux for 5 hr. The phosphorus oxychloride was removed in a rotary evaporator in vacuo. The residue was poured onto ice and the mixture was extracted with 1 liter of ether. The ether solution was dried over $MgSO_4$ and then filtered. The filtrate was taken to dryness in a rotary evaporator yielding 22.9 g of (4-chloro-2-pyrimidinylthio)acetic acid, ethyl ester (an oil). This material was used directly in the next step without purification.

A stirred mixture of 10.0 g of (4-chloro-2-pyrimidinylthio)acetic acid, ethyl ester, 6.0 g of p-chlorobenzylamine and 4.5 g of sodium carbonate in 150 ml. of ethanol was heated under reflux for 5 hr. The reaction mixture was filtered and water was added to the filtrate to induce crystallization. After cooling in ice the precipitate was collected on a filter. Recrystallization from benzene-petroleum ether afforded 5.5 g of product, mp. 175-178°C.

Anal. Calcd for $C_{15}H_{16}N_3O_3ClS$: C, 53.33; H, 4.77, N, 12.44.
Found: C, 53.31; H, 4.77; N, 12.41.

EXAMPLE 34

[4-(p-Chlorobenzyl)methylamino-2-pyrimidinylthio]acetic acid ethyl ester

A mixture of 9.2 g of (4-chloro-2-pyrimidinylthio)acetic acid ethyl ester, 6.2 g of N-methyl-p-chlorobenzylamine and 4.2 g of sodium carbonate in 100 ml. of ethanol was heated under reflux for 5 hr. The reaction mixture was filtered and the filtrate taken to dryness in a rotary evaporator in vacuo. The residual oil was dissolved in about 50 ml. of benzene and petroleum ether was added until the solution became cloudy. On cooling the mixture in ice a precipitate was formed. The precipitate was removed by filtration and recrystallized from ethanol to afford 3.8 g of product, mp. 58°–61°C.

Anal. Calcd for $C_{16}H_{18}N_3O_2SCl$: C, 54.62; H, 5.15; N, 11.94.
Found: C, 54.72; H, 5.25; N, 11.94.

EXAMPLE 35

(4,6-Dichloro-5-methyl-2-pyrimidinylthio)acetic acid, ethyl ester

To a solution of 4.0 g (0.0475 mole) of sodium bicarbonate in 40 ml of water was added with stirring 7.5 g (0.0475 mole) of 5-methyl-2-thiobarbituric acid. Ethyl bromoacetate (7.9 g, 0.0475 mole) was then added and 40 ml of ethanol to make a clear solution. After one-half hour a precipitate was formed. Stirring was continued for one-half hour at room temperature. The precipitate was collected and recrystallized from ethanol to give 6.3 g of (4,6-dihydroxy-5-methyl-2-pyrimidinylthio)acetic acid, ethyl ester mp. 211°–214°C.

Anal. Calcd for $C_9H_{12}N_2O_4S$: C, 44.25; H, 4.95; N, 11.47.
Found: C, 44.53; H, 5.01; N, 11.31.

To a mixture of 25.3 g of (4,6-dihydroxy-5-methyl-2-pyrimidinylthio)acetic acid, ethyl ester in 200 ml of phosphorus oxychloride was slowly added 15.3 g of N,N-diethylaniline. The reaction mixture was heated under reflux for 5 hr. The phosphorus oxychloride was removed in a rotary evaporator and the residue was poured onto 2-liters of ice water. The precipitate was collected and dried. A 5.0 g portion of this solid was recrystallized from petroleum ether to afford 1.7 g of product, mp. 66°–70°C.

Anal. Calcd for $C_9H_{10}Cl_2N_2O_2S$: C, 38.44; H, 3.58; N, 9.96.
Found: C, 38.78; H, 3.59; N, 10.02.

EXAMPLE 36

[4-Chloro-6-(p-chlorobenzylamino)-5-methyl-2-pyrimidinylthio]acetic acid, ethyl ester A stirred mixture of 4.2 g of p-chlorobenzylamine, 3.18 g of sodium carbonate and 8.4 g of (4,6-dichloro-5-methyl-2-pyrimidinylthio)acetic acid, ethyl ester in 100 ml of ethanol was heated under reflux for 4 hr. The reaction mixture was filtered and water was added to the filtrate to start precipitation. The collected solid was recrystallized from benzenepetroleum ether to give 3.6 g of product, mp. 114°–117°C.

Anal. Calcd for $C_{16}H_{17}Cl_2N_3O_2S$: C, 49.75; H, 4.44; N, 10.88.
Found: C, 49.88; H, 4.41; N, 10.88.

EXAMPLE 37

(4-Chloro-6-[p-chlorobenzyl)methylamino]-5-methyl-2-pyrimidinylthio)acetic acid, ethyl ester A stirred mixture of 4.65 g of N-methyl-p-chlorobenzylamine, 3.18 g of sodium carbonate and 8.4 g of (4,6-dichloro-5-methyl-2-pyrimidinylthio)acetic acid, ethyl ester in 100 ml of ethanol was heated under reflux for 5 hr. The reaction mixture was filtred and water was added to the filtrate to the precipitation point. The precipitate was removed by filtration and recrystallized from benzene-petroleum ether to afford 4.1 g of product, mp. 103°–107°C.

Anal. Calcd for $C_{17}H_{19}N_3Cl_2O_2S$: C, 51.00; H, 4.78; N, 10.50.
Found: C, 51.26; H, 4.76; N, 10.35.

EXAMPLE 38

[4-Chloro-6-(2,3-xylidino)-2-pyrimidinylthio]acetic acid, sodium salt, hemihydrate To a solution of 0.46 g of sodium in 150 ml of absolute ethanol was added 6.46 g of [4-chloro-6-(2,3-xylidino)-2-pyrimidinylthio]acetic acid the mixture was stirred at room temperature for 2 hours and the ethanol was then removed on a rotary evaporator. The residue was triturated with anhydrous diethyl ether and the insoluble material was removed by filtration. The crude filter cake was recrystallized twice from ethyl acetate (petroleum ether was used to initiate precipitation) to afford 2.2 g of product, mp. 183°–186°C. (decomp).

Anal. Calc'd for $C_{14}H_{13}N_3O_2ClSNa \cdot 1/2H_2O$: C, 47.39; H, 3.98; N, 11.84.
Found: C, 47.64; H, 3.79; N, 11.52.

What is claimed is:

1. A compound of the formula:

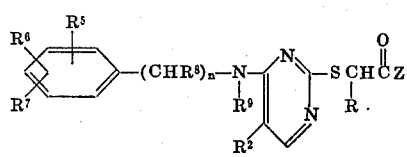

in which

R, $R^2$, $R^7$, $R^8$ and $R^9$ are independently hydrogen or lower alkyl;

$R^5$ is lower alkyl, lower alkoxy, aryl of 6 to 10 carbon atoms, haloaryl of 6 to 10 carbon atoms or halo;

$R^6$ is hydrogen, lower alkyl, halo or lower alkoxy;

n is one of the integers 0, 1, 2 or 3; provided that when n is 0 and $R^5$ is lower alkoxy, $R^6$ is lower alkyl, halo or lower alkoxy; and Z is —OH, —OM, lower alkoxy or —(NH)$_p$—NH$_2$, in which p is one of the integers 0 or 1 and M is an alkali metal, alkaline earth metal or ammonium cation.

2. The compound of claim 1 which is [4-p-chlorobenzylamino)-2-pyrimidinylthio]acetic acid ethyl ester.

3. The compound of claim 1 which is [4-(p-chlorobenzyl)methylamino-2-pyrimidinylthio]acetic acid ethyl ester.

* * * * *